US010617386B2

(12) United States Patent
Kitamura et al.

(10) Patent No.: US 10,617,386 B2
(45) Date of Patent: Apr. 14, 2020

(54) MEDICAL ACOUSTIC COUPLER AND DIAGNOSTIC ULTRASOUND IMAGING APPARATUS

(71) Applicant: Konica Minolta, Inc., Tokyo (JP)

(72) Inventors: Yuiko Kitamura, Hino (JP); Yuichi Nishikubo, Kawasaki (JP)

(73) Assignee: KONICA MINOLTA, INC., Tokyo (JP)

( * ) Notice: Subject to any disclaimer, the term of this patent is extended or adjusted under 35 U.S.C. 154(b) by 250 days.

(21) Appl. No.: 15/135,084

(22) Filed: Apr. 21, 2016

(65) Prior Publication Data

US 2016/0338665 A1 Nov. 24, 2016

(30) Foreign Application Priority Data

May 20, 2015 (JP) .................................. 2015-103056

(51) Int. Cl.
*A61B 8/00* (2006.01)
(52) U.S. Cl.
CPC .......... *A61B 8/4281* (2013.01); *A61B 8/4422* (2013.01); *A61B 8/4405* (2013.01); *A61B 8/4444* (2013.01)
(58) Field of Classification Search
None
See application file for complete search history.

(56) References Cited

U.S. PATENT DOCUMENTS 6,039,694 A * 3/2000 Larson ................. A61B 8/4281
600/459
2006/0264751 A1* 11/2006 Wendelken .......... A61B 8/4281
600/439

(Continued)

FOREIGN PATENT DOCUMENTS

CN 202489974 U * 10/2012
CN 203634205 U * 6/2014

(Continued)

OTHER PUBLICATIONS

Office Action dated Aug. 21, 2018 from Chinese Application No. 201610333416.4 and English translation.

(Continued)

*Primary Examiner* — Pascal M Bui Pho
*Assistant Examiner* — Farouk A Bruce
(74) *Attorney, Agent, or Firm* — Lucas & Mercanti, LLP

(57) ABSTRACT

A medical acoustic coupler is to be detachably attached to an ultrasonic probe including a graspable trunk portion and a protruding portion protruding in a width direction from the trunk portion, the medical acoustic coupler including a sheet-like elastic member, the elastic member including: a contact portion located at a central portion of the elastic member in a planar view, the contact portion being brought into contact with an ultrasound transmission/reception surface located at a top edge of the protruding portion when the elastic member is attached to the ultrasonic probe; and loop portions located on the opposite sides of the contact portion from each other, the loop portions each forming a loop, wherein, when the elastic member is attached to the ultrasonic probe, the loop portions are hooked around the protruding portion, to fix the elastic member to the ultrasonic probe.

11 Claims, 9 Drawing Sheets

(56) References Cited

U.S. PATENT DOCUMENTS

| | | | | |
|---|---|---|---|---|
| 2008/0077211 A1* | 3/2008 | Levinson | ............... | A61F 7/10 607/108 |
| 2009/0005690 A1* | 1/2009 | Irland | ............... | A61B 8/4227 600/472 |
| 2014/0290369 A1* | 10/2014 | Kiyose | ............... | A61B 8/4494 73/632 |

FOREIGN PATENT DOCUMENTS

| | | | |
|---|---|---|---|
| CN | 204293190 U | * | 4/2015 |
| CN | 204293190 U | | 4/2015 |
| JP | H02-092343 A | | 4/1990 |
| JP | H05-277104 A | | 10/1993 |
| JP | 2014193275 A | | 10/2014 |
| WO | 2014132760 A1 | | 9/2014 |

OTHER PUBLICATIONS

Office Action dated Nov. 6, 2018 from the corresponding Japanese Patent Application No. 2015-103056 and English translation.

* cited by examiner

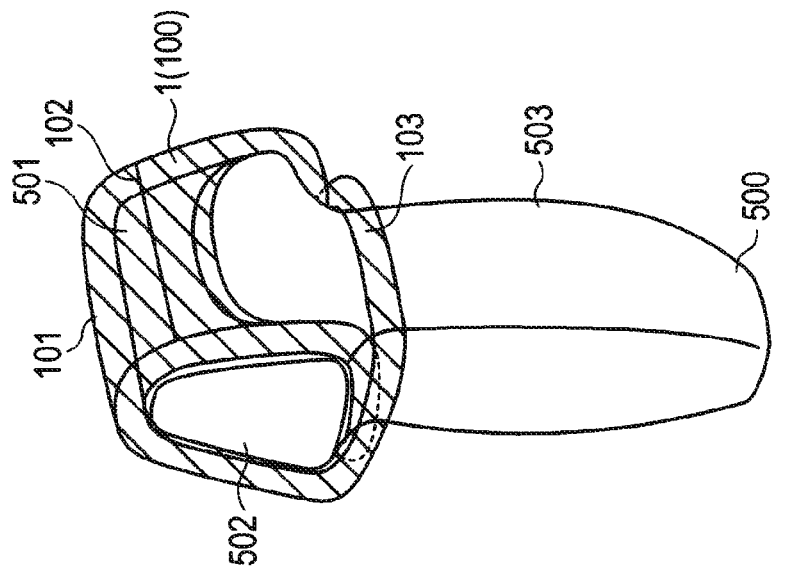
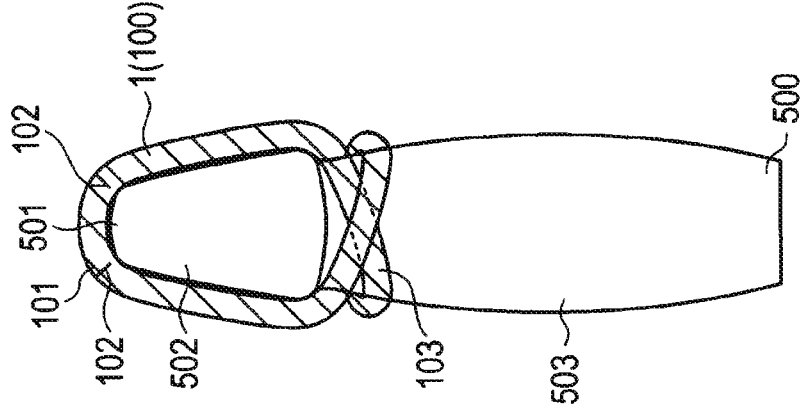
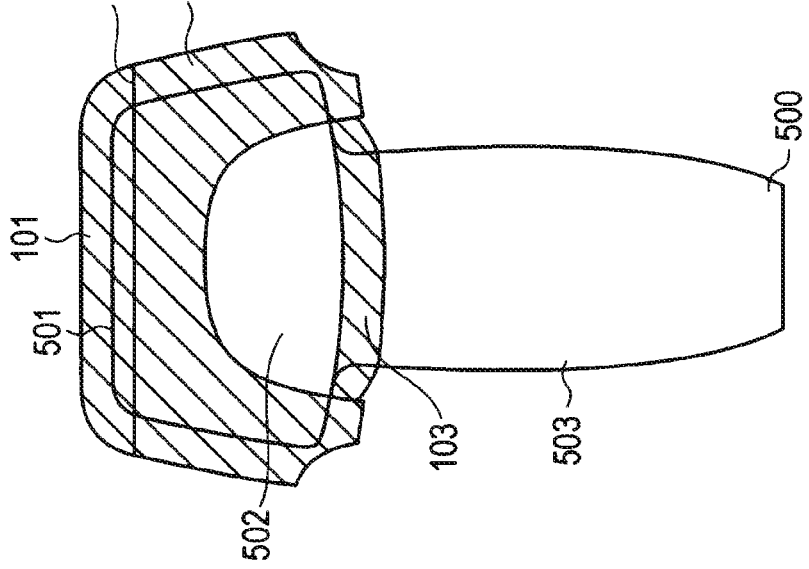

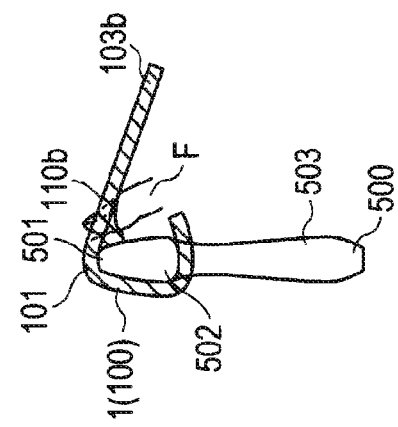
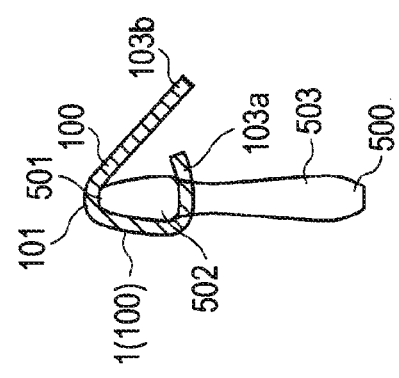
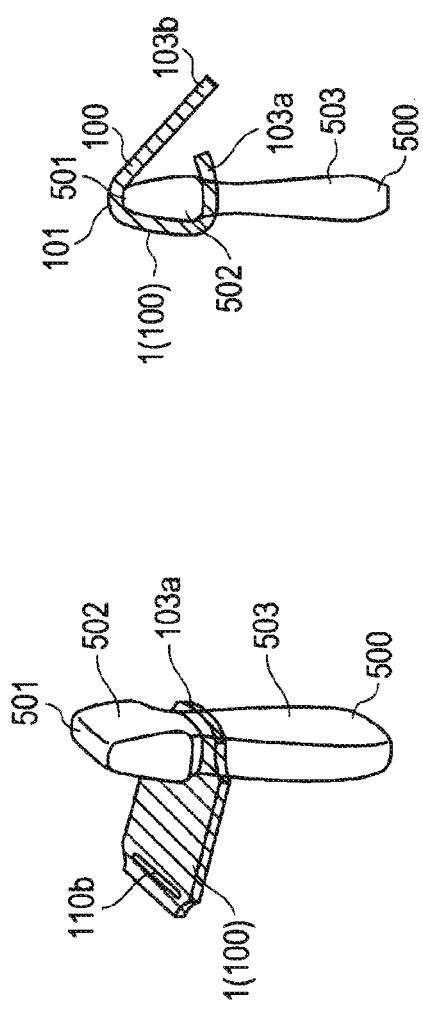
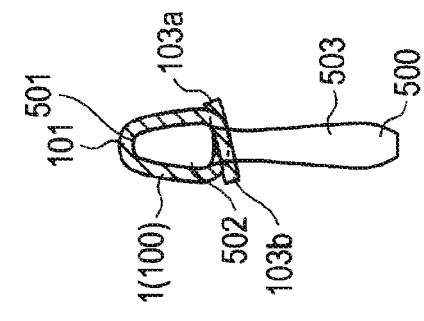
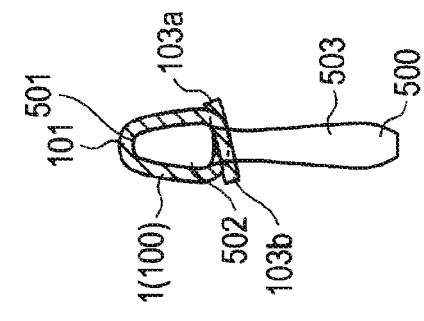
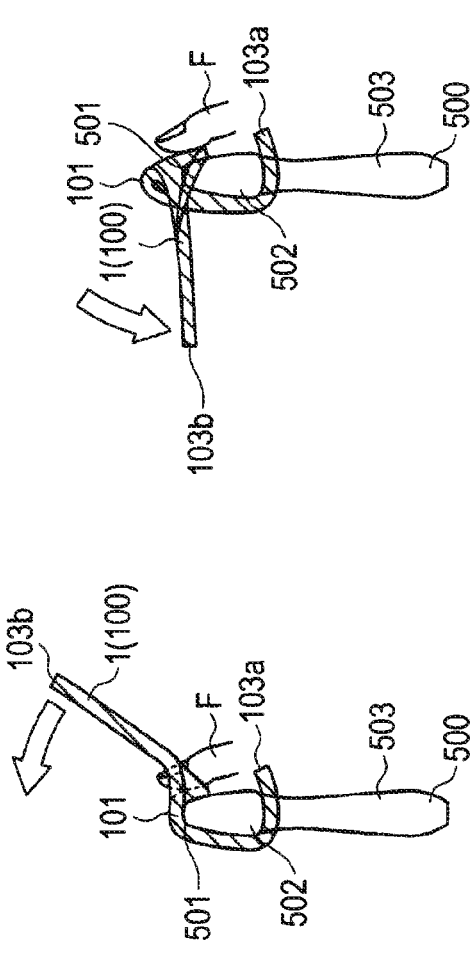

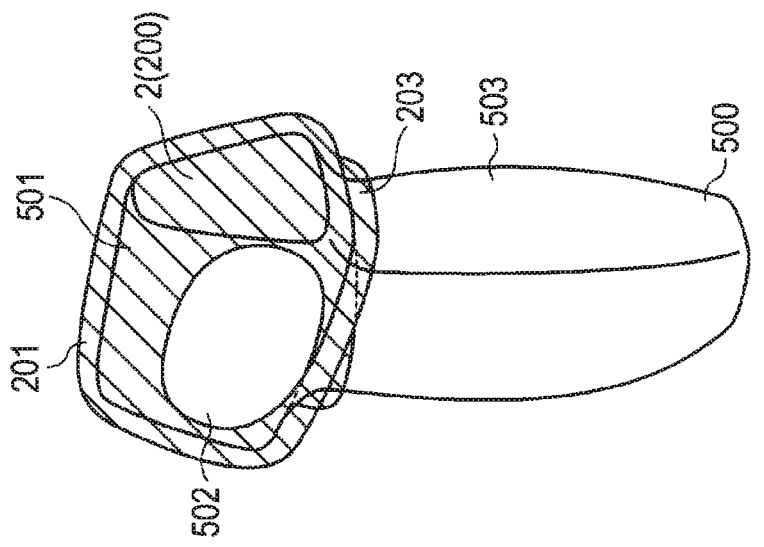
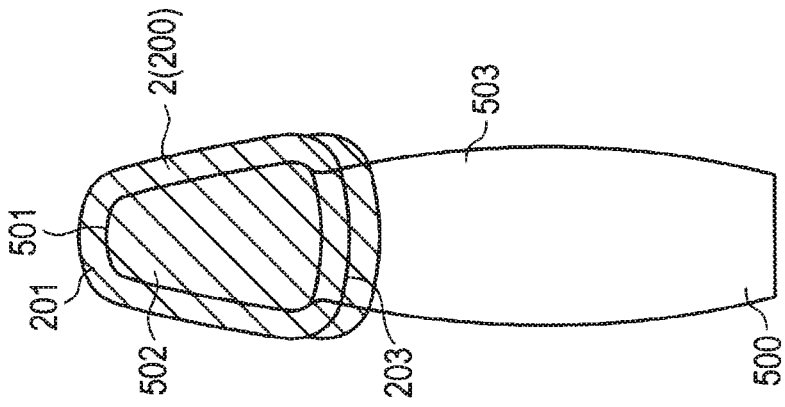
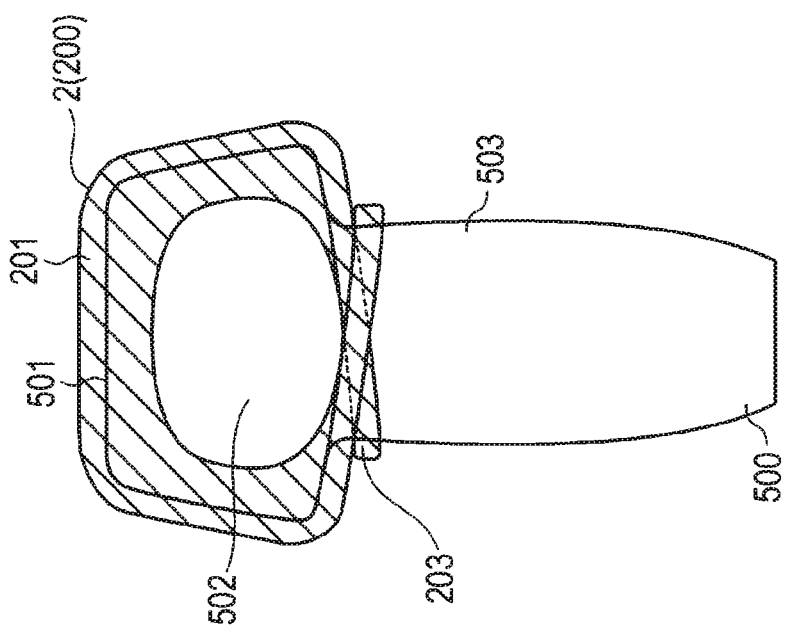

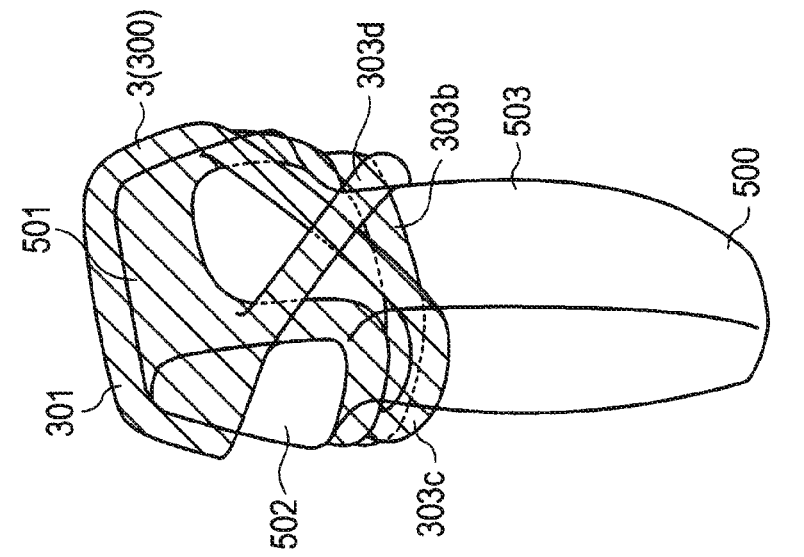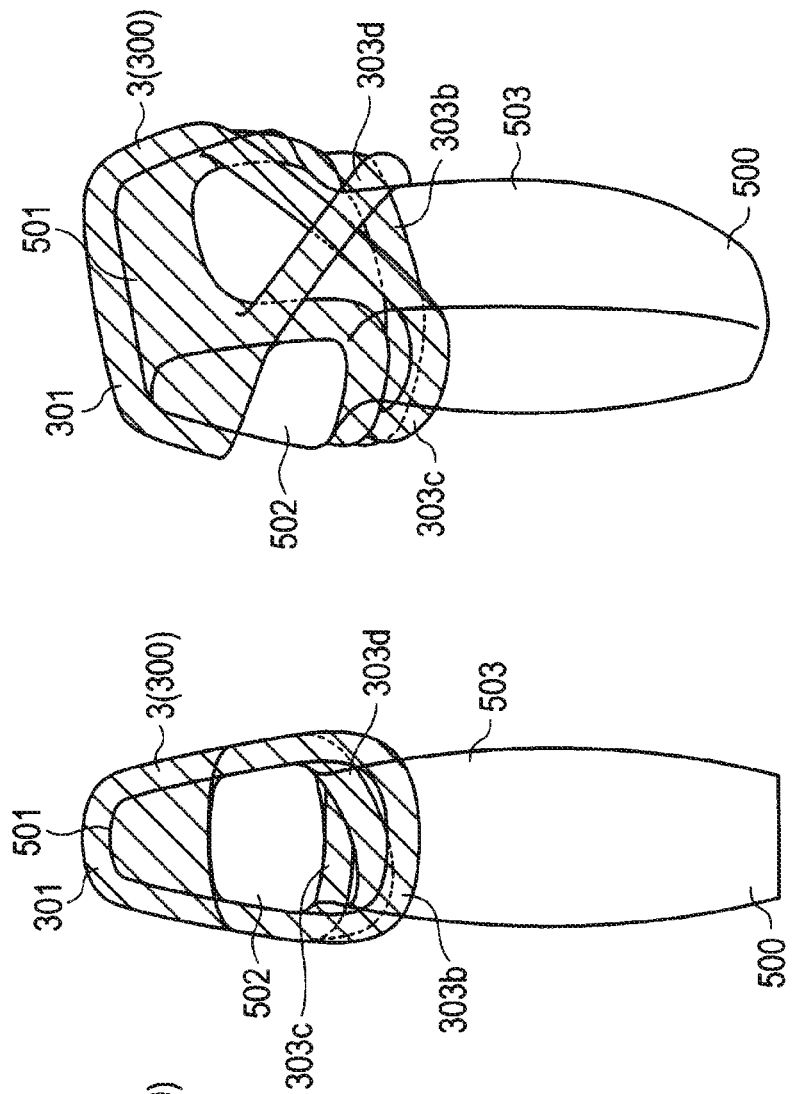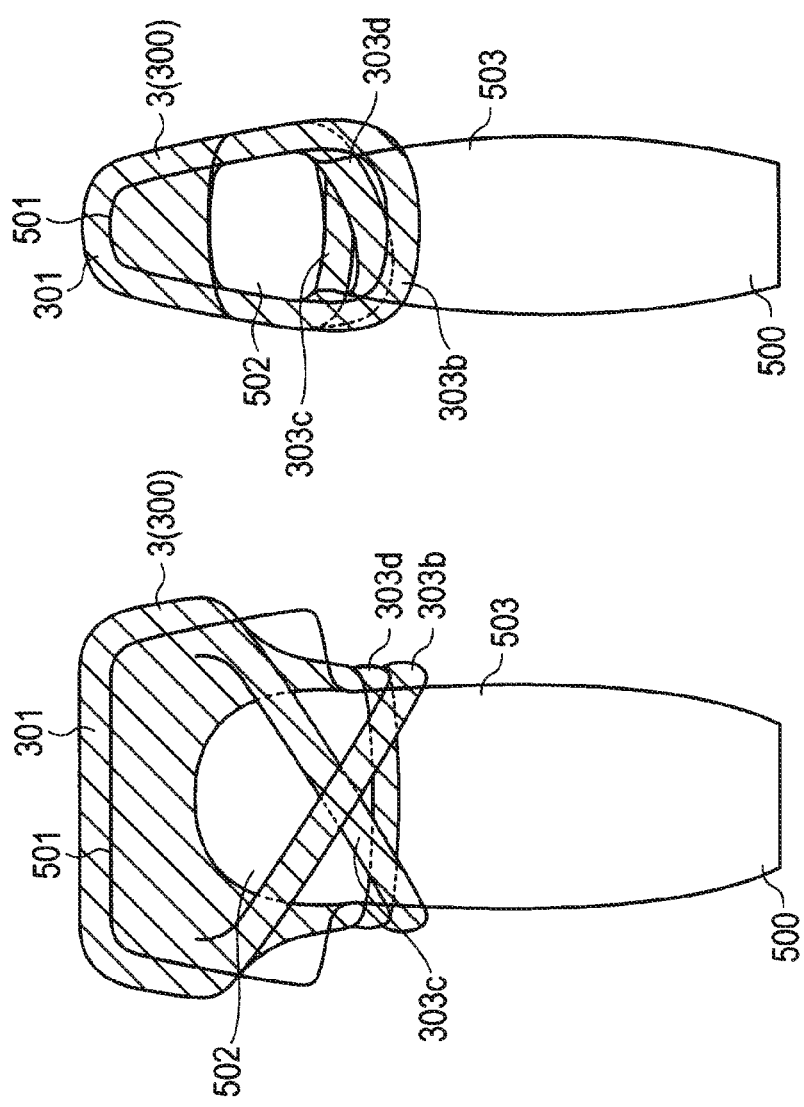

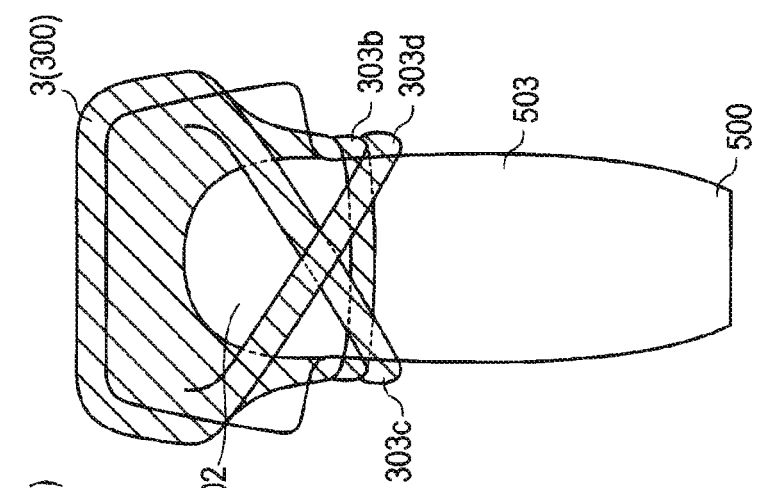
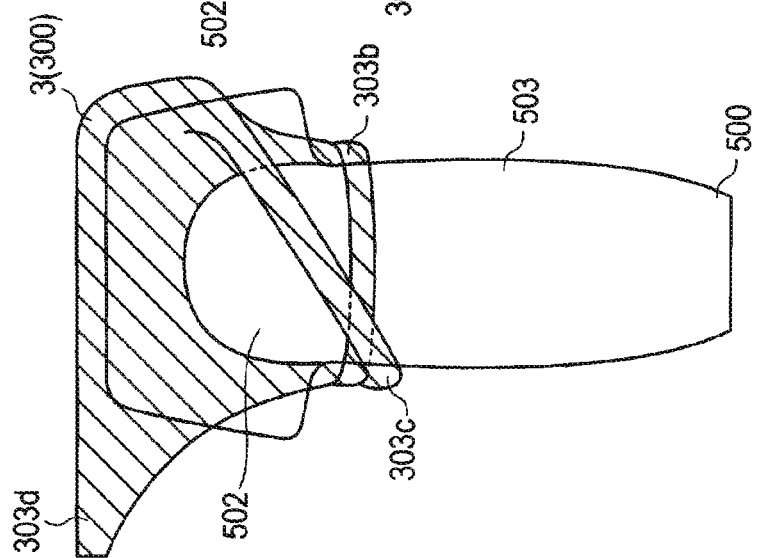
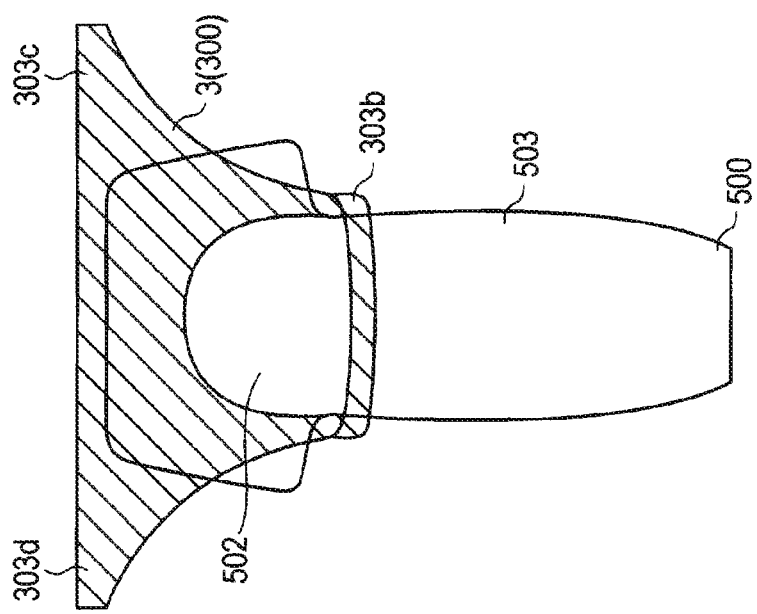

MEDICAL ACOUSTIC COUPLER AND DIAGNOSTIC ULTRASOUND IMAGING APPARATUS

The entire disclosure of Japanese Patent Application No. 2015-103056 filed on May 20, 2015 including description, claims, drawings, and abstract are incorporated herein by reference in its entirety.

BACKGROUND OF THE INVENTION

Field of the Invention

The present invention relates to a medical acoustic coupler to be interposed between an ultrasonic probe and the object being examined at a time of ultrasound imaging by a diagnostic ultrasound imaging apparatus, and to the diagnostic ultrasound imaging apparatus including the medical acoustic coupler.

Description of the Related Art

Diagnostic ultrasound imaging apparatuses of a certain kind are now widely used. A diagnostic ultrasound imaging apparatus of this certain kind transmits ultrasound to a living organism as the object being examined, receives and processes echo signals, and generates images of cross-sections of the object being examined. In such a diagnostic ultrasound imaging apparatus, ultrasonic probes each having an ultrasound transmission/reception surface that transmits and receives ultrasound to and from the object being examined are provided and are normally connected to the main unit of the diagnostic ultrasound imaging apparatus. An ultrasonic pulse is transmitted from the ultrasound transmission/reception surface of an ultrasonic probe brought into contact with the surface of the object being examined, and waves reflected from the object being examined are detected by the ultrasonic probe. The main unit of the diagnostic ultrasound imaging apparatus analyzes the reflected waves, and generates images by performing ultrasound imaging on the object being examined.

If the contact between the ultrasound transmission/reception surface of the ultrasonic probe and the surface of the object being examined is insufficient during the examination, a layer of air might be formed between the ultrasound transmission/reception surface and the surface of the object being examined. If a layer of air is formed between the ultrasound transmission/reception surface and the surface of the object being examined, most ultrasound is reflected by the layer of air, and ultrasound hardly enters the living organism, resulting in incorrect diagnosis. In a case where a superficial site of the object, such as a muscle or a tendon, is examined, ultrasonic beams need to be focused onto the superficial site. In such a case, a medium with a certain thickness is interposed between the ultrasonic probe and the surface of the object being examined, to make adjustment so that the distance between the ultrasonic probe and the site being examined becomes substantially equal to the focus length of ultrasound. In a case where a joint that is bent due to rheumatism or the like is examined, an ultrasonic probe tightly pressed against the joint might cause the patient a great pain due to the uneven surface of the joint. So as not to cause the patient such a pain, an elastic medium should be interposed between the ultrasonic probe and the patient.

In view of the above circumstances, at a time of examination using a diagnostic ultrasound imaging apparatus, an acoustic medium (an acoustic coupler) that has appropriate elasticity and acoustic impedance may be interposed between an ultrasonic probe and the surface of the object being examined. An example of the acoustic medium that has appropriate elasticity and acoustic impedance is a medical acoustic coupler disclosed in JP 2014-193275 A.

JP 2014-193275 A discloses a medical acoustic coupler including: a gel-like layer that has a predetermined thickness and a size corresponding to the ultrasound emitting surface, and is an elastic member that can adhere to the ultrasound emitting surface; and a film layer formed on the contact surface to be brought into contact with a test subject.

In the medical acoustic coupler disclosed in JP 2014-193275 A, the gel-like layer has a predetermined adhesive force. Thus, the medical acoustic coupler is appropriately attached to an ultrasonic probe by virtue of the adhesive force. However, after the medical acoustic coupler is used multiple times, or because dust or the like adheres to the adhesive surface, the adhesive force of the gel-like layer becomes gradually smaller. Due to such a decrease in the adhesive force, the medical acoustic coupler is not fixed to an ultrasonic probe (or is not easily fixed to an ultrasonic probe), and needs to be replaced with a new medical acoustic coupler even if the transmission characteristics of the ultrasound of the medical acoustic coupler have not degraded.

SUMMARY OF THE INVENTION

An object of the present invention is to provide a medical acoustic coupler that can be fixed to an ultrasonic probe without a decrease in the fixing power even after the medical acoustic coupler is used multiple times, and a diagnostic ultrasound imaging apparatus.

To achieve the abovementioned object, according to an aspect, a medical acoustic coupler to be detachably attached to an ultrasonic probe including a graspable trunk portion and a protruding portion protruding in a width direction from the trunk portion, the medical acoustic coupler reflecting one aspect of the present invention comprises a sheet-like elastic member, the elastic member including: a contact portion located at a central portion of the elastic member in a planar view, the contact portion being brought into contact with an ultrasound transmission/reception surface located at a top edge of the protruding portion when the elastic member is attached to the ultrasonic probe; and loop portions located on the opposite sides of the contact portion from each other, the loop portions each forming a loop, wherein, when the elastic member is attached to the ultrasonic probe, the loop portions are hooked around the protruding portion, to fix the elastic member to the ultrasonic probe.

To achieve the abovementioned object, according to an aspect, a diagnostic ultrasound imaging apparatus reflecting one aspect of the present invention comprises: the medical acoustic coupler; and a main unit of the diagnostic ultrasound imaging apparatus, the ultrasonic probe being connected to the main unit, the medical acoustic coupler being to be detachably attached to the ultrasonic probe.

BRIEF DESCRIPTION OF THE DRAWINGS

The above and other objects, advantages and features of the present invention will become more fully understood from the detailed description given hereinbelow and the appended drawings which are given by way of illustration only, and thus are not intended as a definition of the limits of the present invention, and wherein:

FIGS. 3A to 3C are diagrams showing a situation where an elastic member according to the first embodiment of the present invention is fixed to an ultrasonic probe;

FIGS. 4A to 4F are diagrams for explaining a method of attaching the medical acoustic coupler of the first embodiment of the present invention to an ultrasonic probe;

FIGS. 6A to 6C are diagrams showing a situation where an elastic member according to the second embodiment of the present invention is fixed to an ultrasonic probe;

FIGS. 8A to 8C are diagrams showing a situation where an elastic member according to the third embodiment of the present invention is fixed to an ultrasonic probe; and FIGS. 9A to 9C are diagrams for explaining a method of attaching the medical acoustic coupler of the third embodiment of the present invention to an ultrasonic probe.

DESCRIPTION OF THE PREFERRED EMBODIMENTS

Hereinafter, an embodiment of the present invention will be described in detail with reference to the drawings. However, the scope of the invention is not limited to the illustrated examples.

First Embodiment

Figure 1A:
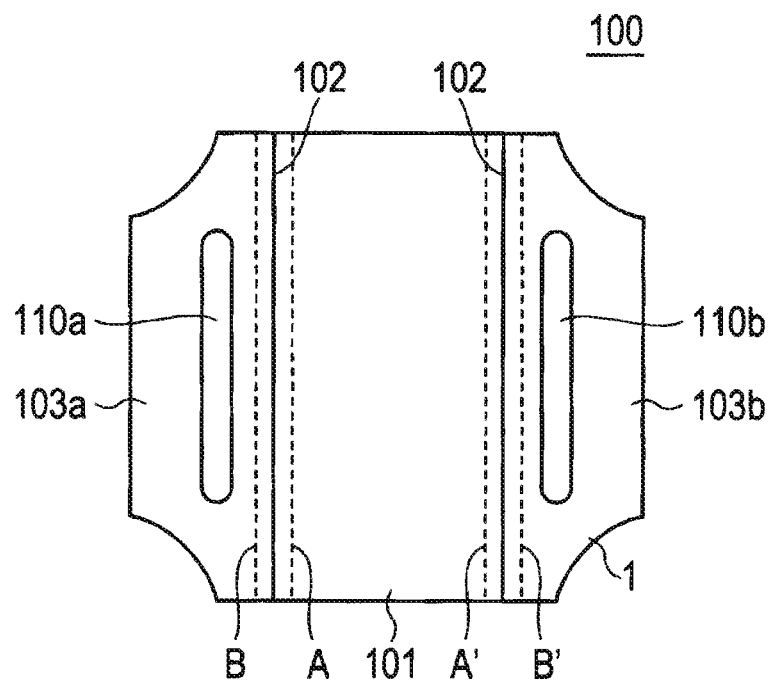
FIGS. 1A and 1B are plan views showing the shape of a medical acoustic coupler according to a first embodiment of the present invention.
Figure 1B:
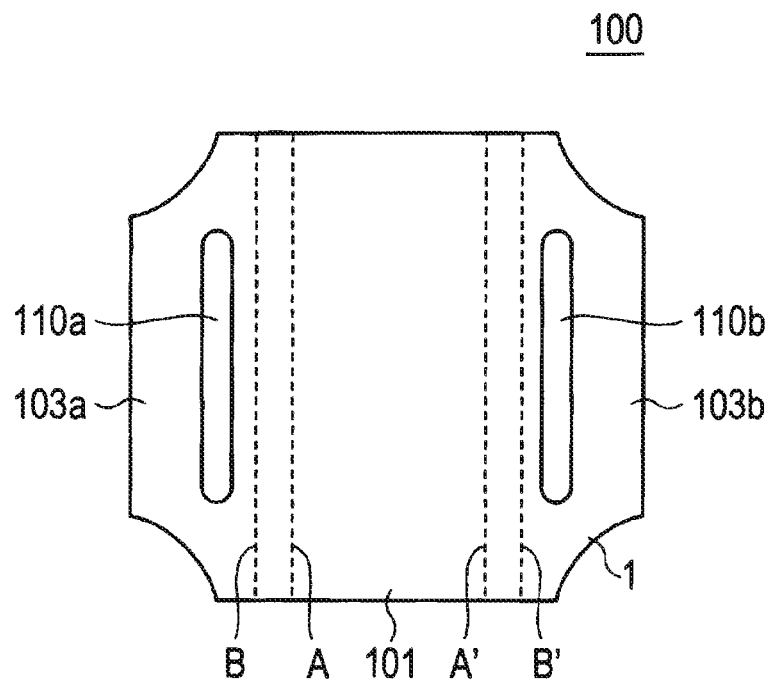
Figure 2:
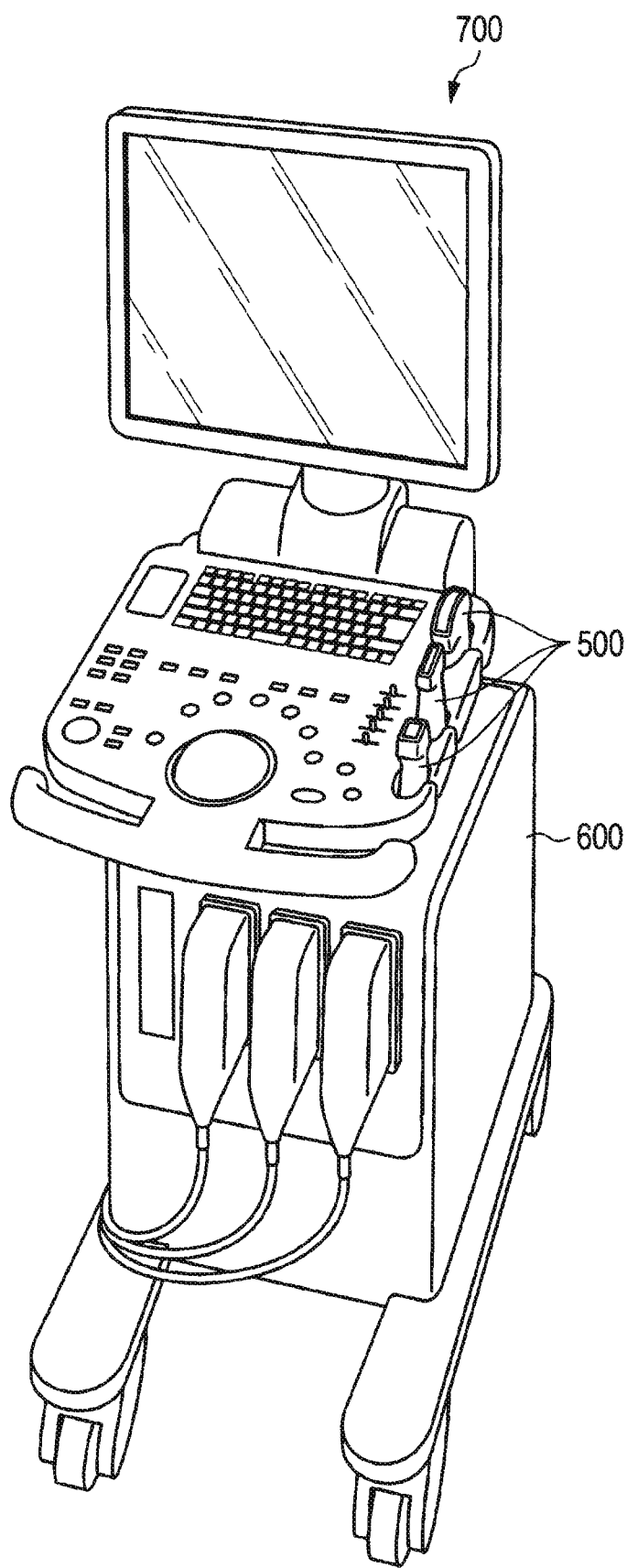
FIG. 2 is a diagram showing an example of a diagnostic ultrasound imaging apparatus that includes an ultrasonic probe to which a medical acoustic coupler according to an embodiment of the present invention is attached.

FIGS. 1A and 1B are plan views showing the shape of a medical acoustic coupler 100 according to a first embodiment of the present invention. The medical acoustic coupler 100 shown in FIGS. 1A and 1B is formed with a sheet-like elastic member 1 made of a material such as an oil-based gel. The medical acoustic coupler 100 is to be attached to an ultrasonic probe 500 of a diagnostic ultrasound imaging apparatus 700 shown in FIG. 2, for example, and is to be used for diagnosis. Ultrasonic probes 500 are designed to be connected to or communicate with the main unit 600 of the diagnostic ultrasound imaging apparatus 700.

As shown in FIGS. 1A and 1B, the elastic member 1 forming the medical acoustic coupler 100 is substantially rectangular in shape, and has two openings 110a and 110b. The elastic member 1 is preferably made of a material that can perform acoustic impedance matching between an ultrasonic probe 500 of the diagnostic ultrasound imaging apparatus 700 and the living organism being examined. Although the shape of the elastic member 1 is substantially rectangular, the corners of the elastic member 1 may be cut off or may be rounded off as shown in FIGS. 1A and 1B, for example. Alternatively, only one corner may be made to have a different shape from the other corners. For example, only one corner may not be cut off while the other corners are cut off. With such a structure, it becomes easier to recognize directionality, and to tell which surface of the elastic member 1 is the front surface and which surface is the back surface. Alternatively, if the surface texturing described later has been performed on one of the surfaces, for example, it is easy to tell which surface is the textured surface, and high user-friendliness is achieved.

The elastic member 1 forming the medical acoustic coupler 100 is made of a material such as an oil-based gel produced by adding a polymeric substance to an oil-phase component, for example. The polymeric substance forming the oil-based gel may be a hydrocarbon-based thermoplastic resin such as a diene-based polymer or a vinyl-based polymer. More specific examples of polymeric substances that can be used to form the elastic member 1 include natural rubber, isoprene rubber, butadiene rubber, styrene-butadiene rubber, chloroprene rubber, polyvinyl chloride, polyacrylic acid, polyacrylate, and polystyrene. Examples of oil-phase components that can be added to such a polymeric substance include paraffin, vegetable oil, animal oil, mineral oil, ester oil, and silicone oil. In embodiments of the present invention, the polymeric substance and the oil-phase component that form the oil-based gel are not limited to any particular substances. Alternatively, a material other than an oil-based gel may be used as the elastic member 1. Since the elastic member 1 is to perform acoustic impedance matching between the ultrasound transmission/reception surface and the living organism as described above, the acoustic impedance of the elastic member 1 is preferably 1.3 to 1.5 MRayl. To maintain a high resolution, the material of the elastic member 1 preferably has a sound speed of approximately 1470 m/s.

The elastic member 1 has a predetermined thickness in a direction perpendicular to the plane of FIGS. 1A and 1B. The thickness of the elastic member 1 is not limited to any particular value in embodiments of the present invention, but is selected in accordance with usage conditions of the medical acoustic coupler 100, for example. Specifically, the focal length from the ultrasound transmission/reception surface of an ultrasonic probe to the site being examined can be adjusted in accordance with the thickness of the elastic member 1. For example, when the site being examined is located near the body surface, the elastic member 1 is thicker than that in a case where the site being examined is not close to the body surface.

Next, the respective components of the medical acoustic coupler 100 are described in detail. As shown in FIGS. 1A and 1B, the medical acoustic coupler 100 includes a contact portion 101, slit portions 102, and loop portions 103.

When the medical acoustic coupler 100 is attached to an ultrasonic probe, the contact portion 101 is brought into contact with the ultrasound transmission/reception surface located at the top edge of the ultrasonic probe, for example. The contact portion 101 is located substantially at the central portion of the rectangular shape of the elastic member 1. Specifically, the contact portion 101 is the portion interposed between dashed lines A and A' in FIGS. 1A and 1B, for example. The dashed lines A and A' are shown for ease of explanation, but are not actually formed.

The size of the contact portion 101 may be determined in accordance with the shape of the ultrasonic probe to which the medical acoustic coupler 100 is to be attached. The width of the contact portion 101 may not be such a width as to completely cover the ultrasound transmission/reception surface. For example, the width of the contact portion 101 may be slightly greater than the width of the ultrasound transmission/reception surface, or may be slightly smaller than the width of the ultrasound transmission/reception surface. If the contact portion 101 is slightly larger than the ultrasound transmission/reception surface, slight deviation of the medical acoustic coupler 100 from the ultrasonic probe can be absorbed, for example. If the contact portion 101 is slightly smaller than the ultrasound transmission/reception surface, formation of blinds at a time of needling, for example, can be prevented.

Where the medical acoustic coupler 100 is attached to an ultrasonic probe, the back surface of the contact portion 101 of the medical acoustic coupler 100 is the portion to be brought into contact with the living organism to be examined. In view of this, surface texturing (wrinkling) is preferably performed on the back surface of the contact portion 101 of the medical acoustic coupler 100, to prevent slippage at a time of screening of a living organism.

The thickness of the elastic member 1 forming the medical acoustic coupler 100 is preferably uniform at least in the portion including the contact portion 101. This is to prevent the bandpass characteristics of ultrasound of the medical acoustic coupler 100 from varying among portions as the thickness of the contact portion 101 varies among portions when the medical acoustic coupler 100 is attached to an ultrasonic probe.

As shown in FIG. 1A, the slit portions 102 are slits formed along the outer longitudinal peripheries of the contact portion 101. In the first embodiment, the slit portions 102 are formed on the outer sides of the dashed lines A and A', as shown in FIGS. 1A and 1B. Because of the slits, the thickness of the medical acoustic coupler 100 at the slit portions 102 is smaller than the thickness at any other portion, particularly at the contact portion 101. With this, the medical acoustic coupler 100 easily bends at the slit portions 102 when the contact portion 101 is attached to an ultrasonic probe. As the slit portions 102 are formed in the back surface of the contact portion 101 of the medical acoustic coupler 100, the front surface of the contact portion 101 easily bends. However, the slit portions 102 are not necessarily formed, and the slit portions 102 are not formed in the structure shown in FIG. 1B. In a case where the slit portions 102 are not formed, it is possible to provide a medical acoustic coupler that can be fixed to an ultrasonic probe without a decrease in the fixing power even after the medical acoustic coupler is used multiple times.

As shown in FIGS. 1A and 1B, in the elastic member 1 forming the medical acoustic coupler 100, the two openings 110*a* and 110*b* are formed near the two sides having the contact portion 101 interposed therebetween. The two openings 110*a* and 110*b* extend along these two sides. As shown in FIGS. 1A and 1B, the openings 110*a* and 110*b* are separated from each other in the short direction of the contact portion 101.

In the medical acoustic coupler 100 according to the first embodiment shown in FIGS. 1A and 1B, the openings 110*a* and 110*b* are designed to have a greater width in the direction parallel to the longitudinal direction of the contact portion 101 than the width in the direction perpendicular to the longitudinal direction of the contact portion 101. Although the openings 110*a* and 110*b* have an elliptical shape in FIGS. 1A and 1B, the shape of the openings 110*a* and 110*b* is not limited to any particular shape in embodiments of the present invention. For example, the shape of the openings 110*a* and 110*b* may be a rectangular shape, or the openings 110*a* and 110*b* may be in the form of small slits each having a much greater width in the direction perpendicular to the longitudinal direction of the contact portion 101 than the width in the direction parallel to the longitudinal direction of the contact portion 101. That is, the openings are through holes that can be slits. In the description below, the openings 110*a* and 110*b* will also be collectively referred to as the openings 110.

Loop portions 103*a* and 103*b* are located near two sides of the outer peripheral sides of the elastic member 1. The two sides are on the opposite sides of the elastic member 1 from each other. At the loop portions 103*a* and 103*b*, loops are formed by the above described openings 110*a* and 110*b*. In FIGS. 1A and 1B, the loop portion 103*a* is a portion closer to the outer edge portion of the elastic member 1 than to the contact portion 101 or the slit portion 102 on the side of the loop portion 103*a* (or a portion closer to the outer edge portion of the elastic member 1 than to a dashed line B in FIGS. 1A and 1B). The loop portion 103*b* is a portion closer to the outer edge portion of the elastic member 1 than to the contact portion 101 or the slit portion 102 on the side of the loop portion 103*b* (or a portion closer to the outer edge portion of the elastic member 1 than to a dashed line B' in FIGS. 1A and 1B). In other words, the openings 110*a* and 110*b* are located substantially at the centers of the loop portions 103*a* and 103*b*, respectively, and loops are formed by the openings 110*a* and 110*b*. In this embodiment, a loop means a closed structure, and is not limited to any particular shape such as a circular shape. When the medical acoustic coupler 100 is attached to an ultrasonic probe, the loop portions 103*a* and 103*b* serve to fix the contact portion 101 to the ultrasound transmission/reception surface while maintaining the contact portion 101 in contact with the ultrasound transmission/reception surface. How the loop portions 103*a* and 103*b* fix the medical acoustic coupler 100 to an ultrasonic probe will be described later in detail. In the description below, the loop portions 103*a* and 103*b* will also be collectively referred to as the loop portions 103. The dashed lines B and B' are shown for ease of explanation, and are not actually formed.

Next, how the elastic member 1 forming the medical acoustic coupler 100 is fixed to an ultrasonic probe 500 is described. FIGS. 3A to 3C are diagrams showing a situation where the elastic member 1 is fixed to an ultrasonic probe 500. FIG. 3A is a front view of the ultrasonic probe 500. FIG. 3B is a side view of the ultrasonic probe 500. FIG. 3C is a perspective view of the ultrasonic probe 500.

As shown in FIG. 3A, at least part of the portion including the ultrasound transmission/reception surface 501 of the ultrasonic probe 500 to which the medical acoustic coupler 100 of the first embodiment is attached has a greater width than the portion designed for grasping the ultrasonic probe 500 when seen from the front. Specifically, in the vicinity of the boundary between the portion including the ultrasound transmission/reception surface 501 and the portion for grasping the probe 500, the width of the portion including the ultrasound transmission/reception surface 501 is greater than the width of the portion for grasping the probe 500 when seen from the front. In the description below, the portion for grasping the ultrasonic probe 500 will be referred to as the trunk portion 503, and the portion protruding from the trunk portion 503, or the portion that includes a portion wider than the trunk portion 503 when seen from the front and includes the ultrasound transmission/reception surface 501, will be referred to as the protruding portion 502. The width direction of the ultrasonic probe 500 is the horizontal direction in FIG. 3A, and is the direction perpendicular to the plane of FIG. 3B. The ultrasonic probe 500 described herein is divided into the trunk portion 503 and the protruding portion 502 for convenience sake, but the trunk portion 503 and the protruding portion 502 are integrally formed in reality. Alternatively, the trunk portion 503 and the protruding portion 502 may be formed separately from each other. The portion having a greater width than the trunk portion 503 when seen from the front may be integrally formed with the protruding portion 502, or may be a separately-formed protrusion joined to the protruding portion 502.

As shown in FIGS. 3A to 3C, the medical acoustic coupler 100 is attached to the ultrasonic probe 500 so that the longitudinal direction of the openings 110 becomes equal to the width direction of the ultrasonic probe 500. Consequently, the expanded openings 110 are located on the front side (and the back side) of the ultrasonic probe 500, as shown in FIG. 3A.

The contact portion 101 of the medical acoustic coupler 100 covers the ultrasound transmission/reception surface 501 of the ultrasonic probe 500, as shown in FIGS. 3A to 3C. The contact portion 101 is fixed to and spreads along the ultrasound transmission/reception surface 501. The portions interposed between the slit portions 102 and the openings 110 of the medical acoustic coupler 100 are fixed to and spread along the sidewall surfaces of the protruding portion 502 of the ultrasonic probe 500. In the medical acoustic coupler 100, the portions including the slit portions 102 are thinner due to the slit portions 102, and accordingly, the medical acoustic coupler 100 easily bends at these portions. With this structure, the contact portion 101 can be more effectively brought into contact with the ultrasound transmission/reception surface 501 when the medical acoustic coupler 100 is attached to the ultrasonic probe 500. Thus, more preferred ultrasound imaging can be performed with the ultrasonic probe 500.

As shown in FIGS. 3A to 3C, the loop portions 103 of the medical acoustic coupler 100 formed with the elastic member 1 are expanded as the protruding portion 502 of the ultrasonic probe 500 is inserted through the openings 110, and are hooked around portions in the vicinities of the boundary between the protruding portion 502 and the trunk portion 503. The portions in the vicinities of the boundary between the protruding portion 502 and the trunk portion 503 are located at two sites on the front and back sides of the ultrasonic probe 500 in the thickness direction. For example, the loop portion 103a is located on the front side while the loop portion 103b is located on the back side (or vice versa). The situation where the medical acoustic coupler 100 is fixed to the ultrasonic probe 500 is further described in detail. The contact portion 101 covers the ultrasound transmission/reception surface 501, and the loop portion 103a and the loop portion 103b are hooked around the expanded portions (which form a portion having a greater width than the trunk portion 503 when seen from the front) of the protruding portion 502 in such a manner that the loop portion 103a and the loop portion 103b cross each other on the side surfaces of the ultrasonic probe 500. As the loop portions 103 formed with the elastic member 1 are expanded, and are hooked around the portions in the vicinities of the boundary between the protruding portion 502 and the trunk portion 503 of the ultrasonic probe 500, the portions of the medical acoustic coupler 100 other than the loop portions 103 are firmly fixed to the ultrasonic probe 500 by virtue of the elastic force. Furthermore, the two loop portions 103a and 103b are hooked around the portions in the vicinities of the boundary between the protruding portion 502 and the trunk portion 503. Thus, the portions of the medical acoustic coupler 100 other than the loop portions 103 can be more firmly fixed to the ultrasonic probe 500.

Next, a method of attaching the medical acoustic coupler 100 to the ultrasonic probe 500 is described. FIGS. 4A to 4F are diagrams for explaining the method of attaching the medical acoustic coupler 100 to the ultrasonic probe 500.

In FIG. 4A, the user inserts the entire protruding portion 502 of the ultrasonic probe 500 through one of the openings 110 of the medical acoustic coupler 100, or through the opening 110a, for example. Since the medical acoustic coupler 100 is formed with the elastic member 1 as described above, the opening 110a easily expands when a force is applied thereto, and returns to its original size when the force is removed. Taking advantage of this feature, the user expands the opening 110a by hand, and inserts the protruding portion 502 through the expanded opening 110a. After moving the portion of the loop portion 103a located between the opening 110a and the outer edge portion of the elastic member 1 to a position in the vicinity of the boundary between the protruding portion 502 and the trunk portion 503, the user pulls his/her hand away from the opening 110a. Of the loop portion 103a, the portion between the opening 110a and the outer edge portion of the elastic member 1, and the portion in the position in the vicinity of the boundary between the protruding portion 502 and the trunk portion 503 will be hereinafter collectively referred to as the one portion of the loop portion 103a.

As a result, the medical acoustic coupler 100 is fixed to the ultrasonic probe 500 by the loop portion 103a. At this point, the protruding portion 502 is inserted through the opening 110a, and the circumference of the opening 110a is substantially in contact with the external surface of the ultrasonic probe 500. That is, the opening 110a of the medical acoustic coupler 100 is smaller than the outer circumference of the portion in the vicinity of the boundary between the protruding portion 502 and the trunk portion 503 of the ultrasonic probe 500. As shown in FIG. 4A, the medical acoustic coupler 100 is attached to the ultrasonic probe 500 so that the longitudinal direction of the opening 110a becomes equal to the width direction of the ultrasonic probe 500.

As shown in FIG. 4B, the user then moves the portion between the opening 110b and the outer edge portion of the elastic member 1 in the loop portion 103b on the other side to the side on which the loop portion 103a is hooked in the thickness direction of the ultrasonic probe 500, while the one portion of the loop portion 103a remains hooked around the portion in the vicinity of the boundary between the protruding portion 502 and the trunk portion 503. Of the loop portion 103b, the portion between the opening 110b and the outer edge portion of the elastic member 1 will be hereinafter referred to as the one portion of the loop portion 103b. Since the one portion of the loop portion 103b is moved over the ultrasound transmission/reception surface 501, the user can easily position the contact portion 101 so that the contact portion 101 following the movement of the one portion of the loop portion 103b completely covers the ultrasound transmission/reception surface 501.

As the one portion of the loop portion 103b is moved to the side on which the one portion of the loop portion 103a of the ultrasonic probe 500 is hooked, the opening 110b shown in FIG. 4A is expanded as shown in FIG. 4B. In the situation shown in FIG. 4C, the user puts a finger F into the opening 110b, and presses the portion of the loop portion 103b facing the outer edge portion of the elastic member 1 via the opening 110b. Of the loop portion 103b, the portion facing the outer edge portion of the elastic member 1 via the opening 110b will be hereinafter referred to as the opening edge portion of the loop portion 103b. In this manner, the positioning performed on the contact portion 101 in FIG. 4B can be confirmed. If the contact portion 101 does not appropriately cover the ultrasound transmission/reception surface 501 in FIG. 4B, the user can adjust the position of the contact portion 101 so that the contact portion 101 can completely cover the ultrasound transmission/reception surface 501.

As shown in FIGS. 4D and 4E, the user then moves the one portion of the loop portion 103b to the opposite side from the side on which the loop portion 103a is hooked in the thickness direction of the ultrasonic probe 500, while continuing to press the opening edge portion of the loop portion 103 with the finger F. In the transition from FIG. 4D to FIG. 4E, the user inserts, through the opening 110b having the finger F inserted therethrough, the contact portion 101 of the medical acoustic coupler 100 and the portion including the entire protruding portion 502 of the ultrasonic probe 500. Like the opening 110a, the opening 110b is smaller than the outer circumference of the portion in the vicinity of the boundary between the protruding portion 502 and the trunk portion 503 of the ultrasonic probe 500. Because of this, when the user releases the one portion of the loop portion 103b while the contact portion 101 of the medical acoustic coupler 100 and the portion including the entire protruding portion 502 of the ultrasonic probe 500 remain inserted through the opening 110b, the medical acoustic coupler 100 is fixed to the ultrasonic probe 500 by the loop portions 103a and 103b as shown in FIG. 4F. More specifically, the loop portion 103a and the loop portion 103b are located on both sides of the ultrasonic probe 500 in the width direction, and the edges of the openings 110a and 110b are substantially in contact with the external surface of the ultrasonic probe 500, as shown in FIG. 4F.

As described above, after the protruding portion 502 is inserted through the opening 110a of the medical acoustic coupler 100, the medical acoustic coupler 100 is bent back, and the protruding portion 502 is inserted through the other opening 110b. In this manner, the medical acoustic coupler 100 can be firmly fixed to the ultrasonic probe 500.

Such a medical acoustic coupler 100 may be manufactured by any of the methods described below. For example, the medical acoustic coupler 100 may be manufactured by injection molding or compression molding using a metal mold having the same planar shape as the medical acoustic coupler 100 shown in FIGS. 1A and 1B. Alternatively, the medical acoustic coupler 100 may be manufactured by performing die-cutting on a large plate (sheet) of the elastic material to be used as the medical acoustic coupler 100.

In a case where the medical acoustic coupler 100 is manufactured by injection molding or compression molding using a metal mold, the openings 110 cannot be shaped into thin, long slits, due to certain restrictions on the molding. Instead, each opening 110 is formed into a rectangular or elliptical shape having a width equal to or greater than a predetermined width. If the openings 110 need to be shaped into slits, the slits should be formed after molding is performed without formation of any openings. Where each opening 110 has a rectangular or elliptical shape with a width equal to or greater than a predetermined width, the medical acoustic coupler 100 does not tear as easily as in a case where each opening 110 is formed as a slit. In view of this, each opening 110 preferably has a rectangular or elliptical shape with a width equal to or greater than a predetermined width.

In a case where the medical acoustic coupler 100 is manufactured by injection molding or compression molding using a metal mold, the width of each slit portion 102 becomes larger due to certain restrictions on the molding. If each slit portion 102 needs to be made thinner, the slit portions 102 should not be formed by the molding. Instead, the slit portions 102 should be formed after the molding of the medical acoustic coupler 100. In a case where the medical acoustic coupler 100 is manufactured by die-cutting, blades that correspond to the slit portions 102 and will not penetrate through the medical acoustic coupler 100 should be added to the mold in advance, so that the slit portions 102 can be formed at the time of manufacturing. Further, in a case where the medical acoustic coupler 100 is manufactured by die-cutting, the openings 110 can be formed into slits, if necessary, without any problem.

As described above, the medical acoustic coupler 100 of the first embodiment is formed with the elastic member 1. The elastic member 1 includes: the contact portion 101 that is located at the central portion of the elastic member 1 in a planar view, and is brought into contact with the ultrasound transmission/reception surface 501 located at the top edge of the protruding portion 502 when the elastic member 1 is attached to an ultrasonic probe 500; and the loop portions 103 that are located on the opposite sides of the contact portion 101 from each other and form loops. When the elastic member 1 is attached to the ultrasonic probe 500, the loop portions 103 are hooked around the protruding portion 502, so that the elastic member 1 is fixed to the ultrasonic probe 500.

With this structure, the medical acoustic coupler 100 is mechanically fixed to the ultrasonic probe 500 by the loop portions 103, and there is no possibility that the medical acoustic coupler 100 is detached while the ultrasonic probe 500 is being used. When the medical acoustic coupler 100 is attached to the ultrasonic probe 500, any fixing tools other than the medical acoustic coupler 100 are not necessary, and the fixing is performed only with the loop portions 103. Thus, the attaching can be readily performed, and the costs for the fixing tools can be lowered.

The medical acoustic coupler 100 is formed with the elastic member 1 made of an oil-based gel or the like, and the loop portions 103 to be used for the fixing easily expand and contract. Thus, the medical acoustic coupler 100 can be appropriately attached to an ultrasonic probe 500 in any shape, and, in this aspect, is highly versatile. Specifically, as long as there is a portion around which the loop portions 103 can be hooked, such as the protruding portion 502 of the ultrasonic probe 500 in the above described first embodiment, the medical acoustic coupler 100 can be easily attached to the ultrasonic probe. Even if the ultrasonic probe does not have any protruding portion around which the loop portions 103 can be hooked, the medical acoustic coupler 100 having the loop portions 103 is formed with the elastic member 1, and accordingly, can be appropriately fixed to the ultrasonic probe, as long as the outer circumference of the ultrasonic probe is sufficiently longer than the openings 110.

The medical acoustic coupler 100 is formed with the elastic member 1 made of an oil-based gel or the like. When the medical acoustic coupler 100 is attached to an ultrasonic probe, the openings 110 forming the loop portions 103 are expanded, and the medical acoustic coupler 100 is fixed to the ultrasonic probe by virtue of the elastic force (the restoring force) of the elastic member 1. As a result, tensile stress generated from the elastic force is applied to the respective portions of the medical acoustic coupler 100 attached to the ultrasonic probe. By virtue of the tensile stress, the medical acoustic coupler 100 is appropriately fixed to the ultrasonic probe, and a problem such as detachment of the contact portion 101 from the ultrasound transmission/reception surface 501 can be avoided.

Since the medical acoustic coupler 100 is formed with the elastic member 1 made of an oil-based gel or the like, the medical acoustic coupler 100 can be washed after use, and be prepared for reuse. The oil-based gel has excellent water-resisting properties, and its elastic modulus hardly changes even after washing with water. Thus, the medical acoustic coupler 100 can be readily washed with water or the like after use, and can be quickly made ready for reuse by drying. In this aspect, the medical acoustic coupler 100 is user-friendly.

Furthermore, the medical acoustic coupler 100 has the slit portions 102 formed along the outer circumference, or more particularly, along both ends of the contact portion 101. At the slit portions 102, the thickness of the elastic member 1 forming the medical acoustic coupler 100 is smaller than the thickness at any other portion. By virtue of the slit portions 102, the contact portion 101 is brought into contact with the ultrasound transmission/reception surface 501 when the medical acoustic coupler 100 is attached to an ultrasonic probe 500, and the peripheral portion of the contact portion 101 can readily spread along the protruding portion 502. As the portions at which the medical acoustic coupler 100 bends are determined beforehand by the slit portions 102, detachment of the contact portion 101 from the ultrasound transmission/reception surface 501 can be avoided.

Second Embodiment

Figure 5:
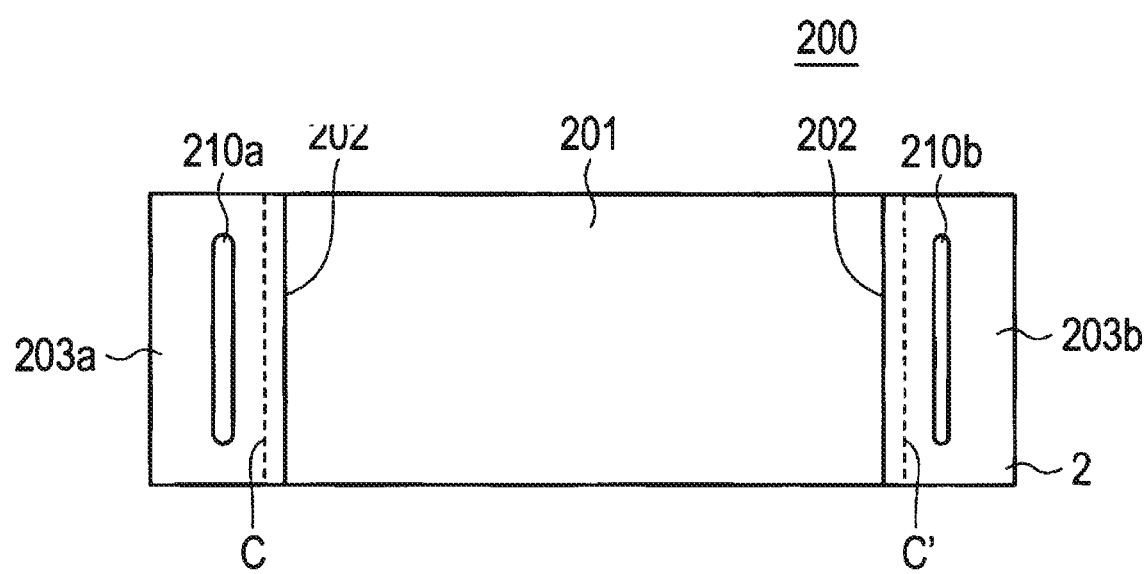
FIG. 5 is a plan view showing the shape of a medical acoustic coupler according to a second embodiment of the present invention.

Next, a medical acoustic coupler 200 according to a second embodiment of the present invention is described. FIG. 5 is a plan view showing the shape of the medical acoustic coupler 200 according to the second embodiment of the present invention.

As shown in FIG. 5, the medical acoustic coupler 200 according to the second embodiment is formed with a sheet-like elastic member 2 made of a material such as an oil-based gel. The medical acoustic coupler 200 is to be fixed to an ultrasonic probe of a diagnostic ultrasound imaging apparatus not shown in FIG. 5, and is to be used for diagnosis.

Like the elastic member 1 of the first embodiment, the elastic member 2 is to perform acoustic impedance matching between the ultrasound transmission/reception surface and a living organism. In view of this, the elastic member 2 is preferably made of a material having an acoustic impedance of approximately 1.3 to 1.5 MRayl. To maintain a high resolution, a material having an internal sound speed of approximately 1470 m/s is also preferable. To sum up, it is preferable to use a material such as an oil-based gel having an acoustic impedance with the above-mentioned value and an internal sound speed with the above-mentioned value, for example. Like the elastic member 1 of the first embodiment, the elastic member 2 can also have its thickness and size changed in accordance with the site to be examined with the medical acoustic coupler 200, the purpose of the examination, and the like.

Although the shape of the elastic member 2 is substantially rectangular in the drawing, the corners of the elastic member 2 may be cut off or may be rounded off, for example. Alternatively, only one corner may be made to have a different shape from the other corners. For example, only one corner may not be cut off while the other corners are cut off. With such a structure, it becomes easier to recognize directionality and tell which surface of the elastic member 2 is the front surface. Alternatively, if the above described surface texturing has been performed on one of the surfaces, for example, it is easy to tell which surface is the textured surface, and high user-friendliness is achieved.

Next, the respective components of the medical acoustic coupler 200 are described. As shown in FIG. 5, the medical acoustic coupler 200 includes a contact portion 201, slit portions 202, and loop portions 203. As described in the first embodiment, the slit portions 202 may not be formed.

When the medical acoustic coupler 200 is attached to an ultrasonic probe, the contact portion 201 is brought into contact with the ultrasound transmission/reception surface located at the top edge of the ultrasonic probe, for example. The contact portion 201 is located substantially at the central portion of the rectangular shape of the elastic member 2. Specifically, the contact portion 201 is the portion interposed between dashed lines C and C' in FIG. 5, for example. The dashed lines C and C' are shown for ease of explanation, but are not actually formed.

As shown in FIG. 5, the slit portions 202 are slits formed along the outer longitudinal peripheries of the contact portion 201. Because of the slits, the thickness of the medical acoustic coupler 200 at the slit portions 202 is smaller than the thickness at any other portion, particularly at the contact portion 201. With this, the medical acoustic coupler 200 easily bends at the slit portions 202 when the contact portion 201 is attached to an ultrasonic probe. As the slit portions 202 are formed in the back surface of the contact portion 201 of the medical acoustic coupler 200, the front surface of the contact portion 201 easily bends.

As shown in FIG. 5, in the elastic member 2 forming the medical acoustic coupler 200, two openings 210a and 210b are formed near the two sides having the contact portion 201 interposed therebetween. The two openings 210a and 210b extend along these two sides. In FIG. 5, the openings 210a and 210b are separated from each other in the longitudinal direction of the contact portion 201. In the description below, the openings 210a and 210b will also be collectively referred to as the openings 210. The shape of the openings 210 is the same as the shape of the openings 110 described in the first embodiment.

Loop portions 203a and 203b are located near two sides of the outer peripheral sides of the elastic member 2. The two sides are on the opposite sides of the elastic member 2 from each other. At the loop portions 203a and 203b, loops are formed by the above described openings 210a and 210b. In FIG. 5, the loop portion 203a is a portion closer to the outer edge portion of the elastic member 2 than to the contact portion 201 or the slit portion 202 on the side of the loop portion 203a (or a portion closer to the outer edge portion of the elastic member 2 than to the dashed line C in FIG. 5). The loop portion 203b is a portion closer to the outer edge portion of the elastic member 2 than to the contact portion 201 or the slit portion 202 on the side of the loop portion 203b (or a portion closer to the outer edge portion of the elastic member 2 than to the dashed line C' in FIG. 5). In other words, the openings 210a and 210b are located substantially at the central portions of the loop portions 203a and 203b, respectively, and loops are formed by the openings 210a and 210b. In this embodiment, a loop means a closed structure, and is not limited to any particular shape such as a circular shape. When the medical acoustic coupler 200 is attached to an ultrasonic probe, the loop portions 203a and 203b serve to fix the contact portion 201 to the ultrasound transmission/reception surface while maintaining the contact portion 201 in contact with the ultrasound transmission/reception surface. How the loop portions 203a and 203b fix the medical acoustic coupler 200 to an ultrasonic probe will be described later in detail. In the description below, the loop portions 203a and 203b will also be collectively referred to as the loop portions 203.

Next, how the elastic member 2 forming the medical acoustic coupler 200 is fixed to an ultrasonic probe 500 is described. FIGS. 6A to 6C are diagrams showing a situation where the elastic member 2 is fixed to an ultrasonic probe 500. FIG. 6A is a front view of the ultrasonic probe 500. FIG. 6B is a side view of the ultrasonic probe 500. FIG. 6C is a perspective view of the ultrasonic probe 500.

As shown in FIG. 6A, at least part of the protruding portion 502 including the ultrasound transmission/reception surface 501 of the ultrasonic probe 500 to which the medical acoustic coupler 200 of the second embodiment is attached has a greater width than the trunk portion 503 when seen from the front, as in the first embodiment. The width direction of the ultrasonic probe 500 is the horizontal direction in FIG. 6A, and is the direction perpendicular to the plane of FIG. 6B.

As shown in FIGS. 6A to 6C, the loop portions 203 of the medical acoustic coupler 200 formed with the elastic member 2 are expanded as the protruding portion 502 of the ultrasonic probe 500 is inserted through the openings 210, and are hooked around portions in the vicinities of the boundary between the protruding portion 502 and the trunk portion 503. In the second embodiment, when the medical acoustic coupler 200 is attached to the ultrasonic probe 500, the orientation of the medical acoustic coupler 200 of the second embodiment differs from the orientation of the medical acoustic coupler 100 of the first embodiment by 90 degrees, as shown in FIGS. 6A to 6C. That is, the medical acoustic coupler 200 is attached to the ultrasonic probe 500 so that the longitudinal direction of the openings 210 becomes equal to the thickness direction of the ultrasonic probe 500, as shown in FIGS. 6A to 6C. The situation where the medical acoustic coupler 200 is fixed to the ultrasonic probe 500 is further described in detail. The contact portion 201 covers the ultrasound transmission/reception surface 501, and the loop portion 203a and the loop portion 203b are hooked around the expanded portions (which form a portion having a greater width than the trunk portion 503 when seen from the front) of the protruding portion 502 in such a manner that the loop portion 203a and the loop portion 203b cross each other on the front surface (shown in FIG. 6A) of the ultrasonic probe 500.

As described above, the medical acoustic coupler 200 according to the second embodiment is attached to an ultrasonic probe 500 so that the longitudinal direction of the openings 210 becomes equal to the thickness direction of the ultrasonic probe 500. Consequently, when the medical acoustic coupler 200 is attached to the ultrasonic probe 500, the side surfaces parallel to the thickness direction of the protruding portion 502 of the ultrasonic probe 500 are almost completely covered with the medical acoustic coupler 200 as shown in FIG. 6B. Thus, shifting of the medical acoustic coupler 200 in a direction parallel to the width direction of the protruding portion 502 of the ultrasonic probe 500 can be prevented while the medical acoustic coupler 200 is attached to the ultrasonic probe 500.

Third Embodiment

Figure 7:
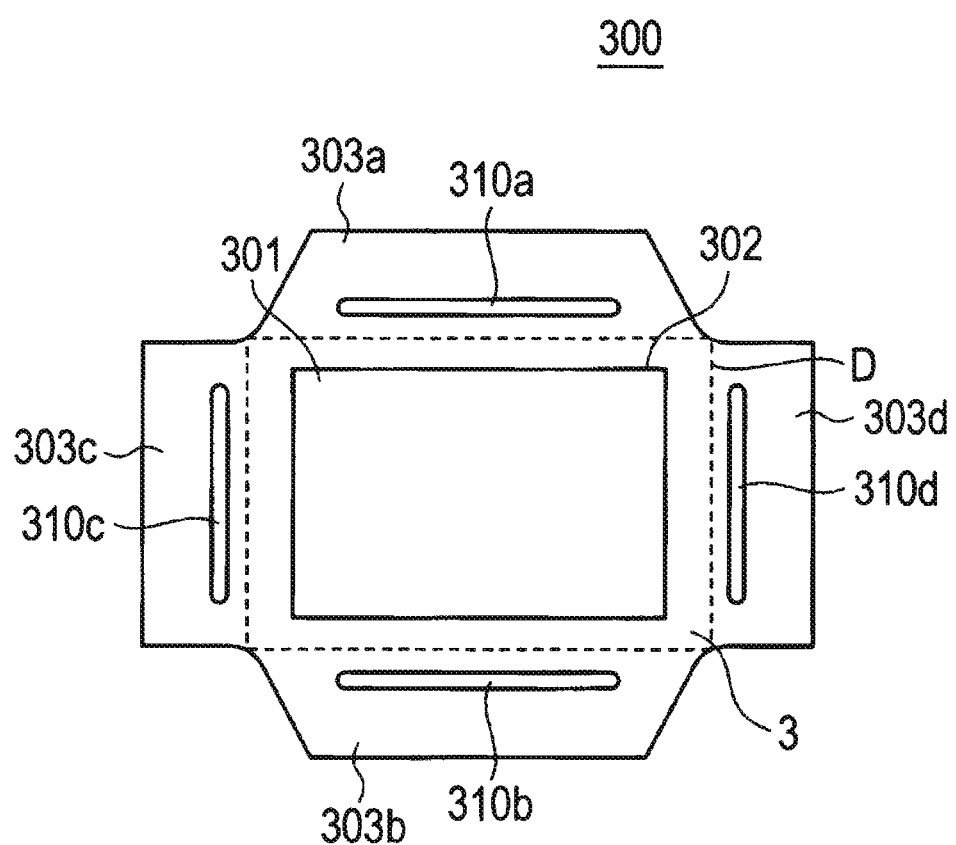
FIG. 7 is a plan view showing the shape of a medical acoustic coupler according to a third embodiment of the present invention.

Next, a medical acoustic coupler 300 according to a third embodiment of the present invention is described. FIG. 7 is a plan view showing the shape of the medical acoustic coupler 300 according to the third embodiment of the present invention.

As shown in FIG. 7, the medical acoustic coupler 300 according to the third embodiment is formed with a sheet-like elastic member 3 made of a material such as an oil-based gel. The medical acoustic coupler 300 is to be fixed to an ultrasonic probe of a diagnostic ultrasound imaging apparatus not shown in FIG. 7, and is to be used for diagnosis.

Like the elastic member 1 of the first embodiment, the elastic member 3 is made of a material such as an oil-based gel having an internal sound speed of approximately 1470 m/s, to perform impedance matching between the ultrasound transmission/reception surface and a living organism. Like the elastic member 1 of the first embodiment, the elastic member 3 can also have its thickness and size changed in accordance with the site to be examined with the medical acoustic coupler 300, the purpose of the examination, and the like.

Although the shape of the elastic member 3 is substantially rectangular in the drawing, the corners of the elastic member 3 may be cut off or may be rounded off, for example. Alternatively, only one corner may be made to have a different shape from the other corners. For example, only one corner may not be cut off while the other corners are cut off. With such a structure, it becomes easier to recognize directionality and tell which surface of the elastic member 2 is the front surface. Alternatively, if the above described surface texturing has been performed on one of the surfaces, for example, it is easy to tell which surface is the textured surface, and high user-friendliness is achieved.

Next, the respective components of the medical acoustic coupler 300 are described. As shown in FIG. 7, the medical acoustic coupler 300 includes a contact portion 301, slit portions 302, and loop portions 303. As described in the first embodiment, the slit portions 302 may not be formed.

When the medical acoustic coupler 300 is attached to an ultrasonic probe, the contact portion 301 is brought into contact with the ultrasound transmission/reception surface located at the top edge of the ultrasonic probe, for example. The contact portion 301 is located substantially at the central portion of the rectangular shape of the elastic member 3. Specifically, the contact portion 301 is the portion surrounded by dashed lines D shown in FIG. 7, for example. The dashed lines D are shown for ease of explanation, but are not actually formed.

As shown in FIG. 7, the slit portions 302 are slits formed along the outer peripheral portions of the contact portion 301. Because of the slits, the thickness of the medical acoustic coupler 300 at the slit portions 302 is smaller than the thickness at any other portion, particularly at the contact portion 301. With this, the medical acoustic coupler 300 easily bends at the slit portions 302 when the contact portion 301 is attached to an ultrasonic probe. As the slit portions 302 are formed in the back surface of the contact portion 301 of the medical acoustic coupler 300, the front surface of the contact portion 301 easily bends.

Loop portions 303a, 303b, 303c, and 303d are portions close to the outer circumference of the elastic member 3. As shown in FIG. 7, the medical acoustic coupler 300 has substantially rectangular protruding regions at the four sides of the contact portion 301 surrounded by the dashed lines D, and the respective four protruding regions are the loop portions 303a to 303d.

Openings 310a to 310d are formed in the loop portions 303a to 303d, respectively. At the respective loop portions 303a to 303d, loops are formed by the openings 310a to 310d. The opening 310a and the opening 310b are formed so that the contact portion 301 is interposed between them, and the opening 310c and the opening 310d are formed so that the contact portion 301 is interposed between them. In this embodiment, a loop means a closed structure, and is not limited to any particular shape such as a circular shape.

When the medical acoustic coupler 300 is attached to an ultrasonic probe, the loop portions 303a to 303d serve to fix the contact portion 301 to the ultrasound transmission/reception surface while maintaining the contact portion 301 in contact with the ultrasound transmission/reception surface. How the loop portions 303a to 303d fix the medical acoustic coupler 300 to an ultrasonic probe will be described later in detail. In the description below, the loop portions 303a to 303d will also be collectively referred to as the loop portions 303. In the description below, the openings 310a to 310d will also be collectively referred to as the openings 310. The shape of the openings 310 is the same as the shape of the openings 110 described in the first embodiment.

Next, how the elastic member 3 forming the medical acoustic coupler 300 is fixed to an ultrasonic probe 500 is described. FIGS. 8A to 8C are diagrams showing a situation where the elastic member 3 is fixed to an ultrasonic probe 500. FIG. 8A is a front view of the ultrasonic probe 500. FIG. 8B is a side view of the ultrasonic probe 500. FIG. 8C is a perspective view of the ultrasonic probe 500.

As shown in FIG. 8A, at least part of the protruding portion 502 including the ultrasound transmission/reception surface 501 of the ultrasonic probe 500 to which the medical acoustic coupler 300 of the third embodiment is attached has a greater width than the trunk portion 503 when seen from the front, as in the first and second embodiments. The width direction of the ultrasonic probe 500 is the horizontal direction in FIG. 8A, and is the direction perpendicular to the plane of FIG. 8B.

As shown in FIGS. 8A to 8C, the loop portions 303 of the medical acoustic coupler 300 formed with the elastic member 3 are expanded as the protruding portion 502 of the ultrasonic probe 500 is inserted through the openings 310, and are hooked around portions in the vicinities of the boundary between the protruding portion 502 and the trunk portion 503. In the third embodiment, as shown in FIGS. 8A to 8C, the protruding portion 502 is fixed from the thickness direction thereof by the loop portions 303a and 303b, and the protruding portion 502 is also fixed from the width direction thereof by the loop portions 303c and 303d. In other words, the medical acoustic coupler 300 is attached to the ultrasonic probe 500 so that the longitudinal direction of the openings 310a and 310b becomes equal to the width direction of the ultrasonic probe 500, and the longitudinal direction of the openings 310c and 310d becomes equal to the thickness direction of the ultrasonic probe 500. The situation where the medical acoustic coupler 300 is fixed to the ultrasonic probe 500 is further described in detail. The contact portion 301 covers the ultrasound transmission/reception surface 501, and the loop portion 303c and the loop portion 303d are hooked around the expanded portions (which form a portion having a greater width than the trunk portion 503 when seen from the front) of the protruding portion 502 in such a manner that the loop portion 303c and the loop portion 303d cross each other on the front surface (shown in FIG. 8A) of the ultrasonic probe 500. The loop portion 303a and the loop portion 303b are hooked around the expanded portions (which form a portion having a greater width than the trunk portion 503 when seen from the front) of the protruding portion 502 in such a manner that the loop portion 303a and the loop portion 303b cross each other on the side surfaces (shown in FIG. 8B) of the ultrasonic probe 500.

That is, the medical acoustic coupler 300 of the third embodiment is designed to be doubly fixed to the ultrasonic probe 500 by the loop portions 303a and 303b (the first loop portions according to an embodiment of the invention) and by the loop portions 303c and 303d (the second loop portions according to an embodiment of the invention). With this structure, the medical acoustic coupler 300 is more firmly fixed to the ultrasonic probe 500, and a problem such as detachment of the contact portion 301 from the ultrasound transmission/reception surface 501 can be avoided.

Next, a method of attaching the medical acoustic coupler 300 of the third embodiment to an ultrasonic probe is described. FIGS. 9A to 9C are diagrams for explaining the method of attaching the medical acoustic coupler 300 of the third embodiment to an ultrasonic probe.

As shown in FIG. 9A, the medical acoustic coupler 300 is first fixed to an ultrasonic probe 500 by the loop portions 303a and 303b so that the side surfaces parallel to the width direction of the protruding portion 502 of the ultrasonic probe 500 are covered, as in the first embodiment. In this stage, the loop portions 303c and 303d are yet to be used for fixing, as shown in FIG. 9A.

As shown in FIG. 9B, one of the loop portions 303c and 303d (the loop portion 303c in FIG. 9B) is then fixed to the ultrasonic probe 500 so that one of the side surfaces parallel to the thickness direction of the protruding portion 502 is covered.

Lastly, as shown in FIG. 9C, the other one of the loop portions 303c and 303d, whichever has not been used in FIG. 9B, is fixed to the ultrasonic probe 500 so that the other one of the side surfaces parallel to the thickness direction of the protruding portion 502. In this manner, the medical acoustic coupler 300 is attached to the ultrasonic probe 500 by the two pairs of loop portions formed with the loop portions 303a to 303d, as shown in FIG. 9C.

As described above, the medical acoustic coupler 300 according to the third embodiment is designed to be doubly fixed to the ultrasonic probe 500 by the loop portions 303a and 303b and by the loop portions 303c and 303d. With this structure, the medical acoustic coupler 300 is more firmly fixed to the ultrasonic probe 500, and a problem such as detachment of the contact portion 301 from the ultrasound transmission/reception surface 501 can be avoided.

Although preferred embodiments of the present invention have been described so far, the present invention is not limited to those embodiments. In each of the examples described in the above embodiments, the contact portion 101 (201, 301) and the loop portions 103 (203, 303) are formed with the same elastic member 1 (2, 3). However, the present invention is not limited to that, and the loop portions forming loops may be attached to portions located in the vicinities of the outer circumference of a rectangular contact portion, for example. In that case, the loop portions forming loops may be formed with string-like or cord-like elastic members, for example, and the loop portions may be connected to portions located near the respective corners of the rectangular contact portion. Alternatively, loop portions in the form of handles may be connected to the contact portion, for example.

The present invention is suitable for a medical acoustic coupler attached to an ultrasonic probe in a diagnostic ultrasound imaging apparatus.

Although the present invention has been described and illustrated in detail, it is clearly understood that the same is by way of illustrated and example only and is not to be taken byway of limitation, the scope of the present invention being interpreted by terms of the appended claims.

What is claimed is:

1. A medical acoustic coupler to be detachably attached to an ultrasonic probe, the ultrasonic probe including a graspable trunk portion and a protruding portion protruding in a width direction from the trunk portion, the protruding portion having an ultrasound transmission/reception surface, wherein the medical acoustic coupler comprises:

an elastic member in the form of a sheet,
the elastic member including:
a contact portion located at a central portion of the elastic member in a planar view, the contact portion being brought into contact with the ultrasound transmission/reception surface located at a top edge of the protruding portion when the elastic member is attached to the ultrasonic probe; and loop portions located on opposite sides of the contact portion from each other, the loop portions having openings through the elastic member in a thickness direction of the elastic member, each of the openings forming a loop, a circumference of the each of the openings being smaller than an outer circumference of the ultrasonic probe at a boundary between the protruding portion and the graspable trunk portion in an unexpanded state of the loop portions,
wherein, the loop portions of the elastic member are configured to be hooked around the protruding portion to fix the elastic member to the ultrasonic probe and hold the contact portion of the elastic member to the ultrasonic probe.

2. The medical acoustic coupler according to claim 1, wherein, when attached to the ultrasonic probe, the elastic member is fixed to the ultrasonic probe as the loop portions cross each other and are hooked around the protruding portion.

3. The medical acoustic coupler according to claim 1, wherein the elastic member is made of a material containing an oil-based gel as a principal component.

4. The medical acoustic coupler according to claim 1, wherein surface texturing is performed on the contact portion at the side to be in contact with a living organism during use.

5. The medical acoustic coupler according to claim 1, wherein the loop portions are separated from each other in a short direction of the contact portion, and an opening is formed at a central portion of each of the loop portions, the opening extending in a longitudinal direction of the contact portion.

6. The medical acoustic coupler according to claim 1, wherein the loop portions are separated from each other in a longitudinal direction of the contact portion, and the opening of the each of the loop portions extending in a short direction of the contact portion.

7. The medical acoustic coupler according to claim 1, wherein
the loop portions include first loop portions and second loop portions,
the first loop portions are separated from each other in a short direction of the contact portion, an opening being formed at a central portion of each of the loops formed by the first loop portions, the opening extending in a longitudinal direction of the contact portion, and
the second loop portions are separated from each other in the longitudinal direction of the contact portion, an opening being formed at a central portion of each of the loops formed by the second loop portions, the opening extending in the short direction of the contact portion.

8. The medical acoustic coupler according to claim 1, wherein the elastic member further includes slit portions respectively disposed between the contact portion and each of the loop portions, a thickness of the elastic member at the slit portions is thinner than a thickness of the contact portion.

9. A diagnostic ultrasound imaging apparatus comprising:
the medical acoustic coupler according to claim 1; and
a main unit of the diagnostic ultrasound imaging apparatus, the ultrasonic probe being connected to the main unit, the medical acoustic coupler being to be detachably attached to the ultrasonic probe.

10. The medical acoustic coupler according to claim 1, wherein the slit portions include slits formed on a back surface of the contact portion, the back surface facing away from the ultrasonic probe when the elastic member is attached to the ultrasonic probe.

11. The medical acoustic coupler according to claim 8, wherein the thickness of the elastic member at the slit portions is thinner than the thickness of the contact portion and a thickness of the loop portion.

* * * * *